(12) United States Patent
Lombez et al.

(10) Patent No.: US 10,302,574 B2
(45) Date of Patent: May 28, 2019

(54) METHOD FOR ANALYSING THE CRYSTAL STRUCTURE OF A POLYCRYSTALLINE SEMICONDUCTOR

(71) Applicants: Centre National de la Recherche Scientifique—CNRS, Paris (FR); ELECTRICITÉ DE FRANCE—EDF, Paris (FR)

(72) Inventors: Laurent Lombez, Nanterre (FR); Jean-François Guillemoles, Paris (FR); Amaury Delamarre, Paris (FR)

(73) Assignees: CENTRE NATIONAL DE LA RECHERCHE SCIENTIFIQUE—CNRS, Paris (FR); ELECTRICITÉ DE FRANCE—EDF, Paris (FR)

( * ) Notice: Subject to any disclaimer, the term of this patent is extended or adjusted under 35 U.S.C. 154(b) by 1116 days.

(21) Appl. No.: 14/419,022

(22) PCT Filed: Jul. 30, 2013

(86) PCT No.: PCT/EP2013/066043
§ 371 (c)(1),
(2) Date: Feb. 2, 2015

(87) PCT Pub. No.: WO2014/020046
PCT Pub. Date: Feb. 6, 2014

(65) Prior Publication Data
US 2015/0212011 A1   Jul. 30, 2015

(30) Foreign Application Priority Data
Aug. 2, 2012 (FR) ..................... 12 57556

(51) Int. Cl.
*G01N 21/95* (2006.01)
*G01N 21/64* (2006.01)
(Continued)

(52) U.S. Cl.
CPC ......... *G01N 21/95* (2013.01); *G01N 21/6445* (2013.01); *G01N 21/6489* (2013.01);
(Continued)

(58) Field of Classification Search
CPC ........... G01N 21/9501; G01N 21/6445; G01N 21/6489; G01N 2021/646; G01N 21/95; G01N 2201/06113; G01N 2201/12
See application file for complete search history.

(56) References Cited

U.S. PATENT DOCUMENTS

| 8,301,409 B2 * | 10/2012 | Ahmad | G01R 31/308 250/200 |
| 2010/0150428 A1 | 6/2010 | Andreev et al. | |
| 2013/0126756 A1 * | 5/2013 | Xu | G01N 21/6408 250/459.1 |

FOREIGN PATENT DOCUMENTS

| JP | 2008224476 A | 9/2008 |
| JP | 2010174181 A | 8/2010 |
| WO | 03/041123 A2 | 5/2003 |

OTHER PUBLICATIONS

M. Suezawa et al., Radiative Recombination on Dislocations of Silicon Crystals, Jul. 7, 1981, Japanese Journal of Applied Physics, vol. 20, No. 7, pp. 29-30.*
(Continued)

*Primary Examiner* — Mischita L Henson
(74) *Attorney, Agent, or Firm* — Osha Liang LLP

(57) ABSTRACT

A method for analyzing the crystal structure of a polycrystalline semiconductor material is described. According to one embodiment, the method includes exciting the material to make the material emit a luminescent signal, detecting, at each point of a mesh in a preset spatial region of the material, the luminescent signal at a variable polarization angle, in a frequency band of width greater than or equal to the width of the bandgap of the material, estimating, at each
(Continued)

point of the mesh in the preset spatial region of the material, from the signal detected for said point of the mesh, a data characteristic of the modulation of the luminescent signal, modelled by a sum of sine waves, as a function of the polarization angle, and representing the characteristic data over all of the points of the mesh in the preset spatial region.

13 Claims, 4 Drawing Sheets

(52) U.S. Cl.
CPC ... *G01N 21/9501* (2013.01); *G01N 2021/646* (2013.01); *G01N 2201/06113* (2013.01); *G01N 2201/12* (2013.01)

(56) References Cited

OTHER PUBLICATIONS

G. Kato et al., Polarized photolumniescence imaging analysis around small-angle grain boundaries in multicrystalline silicon waters for solar cells, 2014, Japanese Jounal of Applied Physics, vol. 53, pp. 080303-1-080303-3.*

M. Peloso, Polarization analysis of luminescence for the characterization of silicon wafer solar cells, 2011, Applied Physics Letters, vol. 98, pp. 32-35.*

W. M. Duncan et al., Fourier Transform Photoluminescence Analysis of Semiconductor Materials, 1987, Proc. of SPIE Raman and Luminescence Spectroscopy, vol. 822 pp. 172-180.*

D. Lausch et al., Classification of crystal defects in multicrystalline silicon solar cells and wafer using spectrally and spatially resoved pholuminescence, 2016, Journal of Applied Physics, vol. 119, pp. 054501-1 to 054501-6.*

Office Action issued in counterpart Japanese Patent Application No. 2015-524769, dated Apr. 11, 2017 (6 pages).

M. Peloso, et al; "Polarization analysis of luminescence for the characterization of silicon wafer solar cells;" Applied Physics Letters, AIP, American Institute of Physics, vol. 98, No. 17; XP012140460; Apr. 29, 2011; pp. 171914-1-171914-3 (3 pages).

M. Chamarro, et al.; "Photoluminescence polarization of semiconductor nanocrystals;" Journal of Luminescence, vol. 70; XP002688507; 1996; pp. 222-237 (16 pages).

International Search Report for corresponding International Application No. PCT/EP2013/066043, dated Sep. 11, 2013 (3 pages).

Written Opinion for corresponding International Application No. PCT/EP2013/066043, dated Sep. 11, 2013 (6 pages).

* cited by examiner

METHOD FOR ANALYSING THE CRYSTAL STRUCTURE OF A POLYCRYSTALLINE SEMICONDUCTOR

The present invention relates to techniques for analysing the crystal structure of polycrystalline semiconductor materials, and particularly to techniques for characterizing the structure of polycrystalline absorber materials used in photovoltaic cells.

The attractiveness of photovoltaic energy as an alternative to fossil fuels has given rise to the development of products such as solar panels employing many photovoltaic cells.

The development of the market for photovoltaic products has revitalized research and development in this field, and part of this research and development effort has been concentrated on the development of methods for characterizing the materials used in order to improve existing products and to pave the way for new generations of products. Furthermore, the boom in these markets has made it necessary to define tests of quality and compliance with expected performance (particularly in terms of conversion efficiency) and to develop procedures for testing and analysing performance, which procedures have to be compatible with the demands of mass production.

This is notably the case with photovoltaic cells based on polycrystalline semiconductor materials, for which techniques for detecting defects in the crystal structure or microstructure have been developed. For example, the article "Polarization analysis of luminescence for the characterization of silicon wafer solar cells" by M. Peloso, B. Hoex and A-G. Aberle (Applied Physics Letters 98, 171914 (2011)) describes a method for analysing defects in a photovoltaic cell by analysing the polarization of an electroluminescent signal emitted by the analysed cell.

Apart from detection of defects, techniques for characterizing the structure or microstructure of polycrystalline materials have also been developed. The structure or microstructure of polycrystalline materials is generally characterized using a scanning electron microscope operating in EBSD (electron backscatter diffraction) mode, or else using a TEM (transmission electron microscope). These material characterization tools are for heavy use since samples to be analysed require preparation, which can prove difficult, thereby making them incompatible with the requirement for quality and compliance testing in the mass production context. Specifically, to use these techniques it is necessary to prepare the sample to be analysed by polishing its surface in order to eliminate roughness. This preparation can be tricky to implement and analysis of the sample is sometimes impossible due, for example, to problems relating to the work-hardening generated by the material polishing step.

The technique of polarized Raman spectra mapping may also be considered for the purpose of characterizing the structure or microstructure of polycrystalline materials, but in practice it is expensive as it necessitates a laser of high spectral quality and a very high-resolution spectrometer.

One aim of the present invention is to solve the drawbacks of the techniques for characterizing polycrystalline materials outlined above.

The invention thus provides a method for analysing the crystal structure of a polycrystalline semiconductor material, comprising exciting the material in order to make the material emit a luminescent signal, detecting, at each point of a mesh in a preset spatial region of the material, the luminescent signal at a variable polarization angle, in a frequency band of width greater than or equal to the width of the bandgap of the material, estimating, at each point of the mesh in the preset spatial region of the material, from the signal detected for said point of the mesh, a data characteristic of the modulation of the luminescent signal modelled by a sum of sine waves, as a function of the polarization angle, and generating a representation of the characteristic data over all the points of the mesh in the preset spatial region.

The proposed method has the advantage of enabling simple, rapid and inexpensive characterization of the structural properties of polycrystalline materials, in comparison with the aforementioned techniques. In particular, the proposed method is non-destructive (it does not degrade the sample) and requires no sample preparation. It is therefore possible to reuse the sample once it has been analysed, to analyse a sample during manufacture (for example, for a photovoltaic cell, during the process of growing the material via deposition on a substrate, to verify that the growth process gives a priori satisfactory results). The proposed method is therefore particularly suited to the demands of mass production, since it enables the in situ analysis and testing of the products at all stages of manufacture.

The proposed method may advantageously be implemented with a model of the modulated luminescent signal of the form: $I_{lum} = A_0 + \Sigma_{k=(1 \ldots K)} A_k \cdot \sin(n_k \theta + \varphi_k)$, where $I_{lum}$ represents the intensity of the luminescent signal, $A_k$ is an amplitude parameter of the luminescent signal, $\theta$ represents the analysis angle of the polarization of the luminescent signal, $\varphi_k$ is a parameter of the phase shift of the luminescent signal with respect to a phase reference, $A_0$ a parameter representing the minimum value of the intensity of the luminescent signal, $n_k$ being a strictly positive integer, and k is a natural integer summation index ranging from 1 to K, and in which the estimated characteristic data corresponds to the amplitude, phase shift, frequency and/or minimum value parameter, or to one of their combinations.

It is moreover possible to consider detecting the luminescent signal by means of a camera, the mesh in the preset spatial region then corresponding by choice with the points on the sensor of the camera.

In a first embodiment of the method, optical excitation is used in order to generate by photoluminescence the luminescent signal emitted by the material.

In a second embodiment of the method, electrical excitation is used in order to generate by electroluminescence the luminescent signal emitted by the material.

In a third embodiment of the method, thermal heating of the material is used in order to generate by thermoluminescence the luminescent signal emitted by the material.

According to another aspect, provision is made for a system for analysing the crystal structure of a polycrystalline semiconductor material, which comprises means for exciting the material arranged to excite the material in order to make the material emit a luminescent signal, a means for detecting, at each point of a mesh in a preset spatial region of the material, the luminescent signal at a variable polarization angle, in a frequency band of width greater than or equal to the width of the bandgap of the material, and a data processing unit, comprising a computer processor operationally coupled to memory means and to an input/output interface module, the memory means being configured to store data corresponding to the signal detected for each point of the mesh, an analyser, which is executed by the computer processor and configured to estimate, at each point of the mesh in the preset spatial region of the material, from the signal detected for said point of the mesh, a data characteristic of the modulation, of the luminescent signal modelled by a sum of sine waves, as a function of the polarization angle; and to generate a representation of the characteristic data over all of the points of the mesh in the preset spatial region.

In an embodiment, the analyser of the analying system is furthermore configured to estimate a characteristic data as a function of a model of the modulated luminescent signal of the form: $I_{lum} = A_0 + \Sigma_{k=(1 \ldots K)} A_k \cdot \sin(n_k \theta + \varphi_k)$, where $I_{lum}$ represents the intensity of the luminescent signal, $A_k$ is an amplitude parameter of the luminescent signal, $\theta$ represents the analysis angle of the polarization of the luminescent signal, $\varphi_k$ is a parameter of the phase shift of the luminescent signal with respect to a phase reference, $A_0$ a parameter representing the minimum value of the intensity of the luminescent signal, $n_k$ being a strictly positive integer, and k is an integer summation index ranging from 1 to K, and in which the estimated characteristic data corresponds to the amplitude, phase shift, frequency and/or minimum value parameter, or to one of their combinations.

According to an embodiment, the detecting means of the analysing system comprises a camera, the preset spatial region mesh on the material then advantageously being chosen to correspond to points on the sensor of the camera.

Moreover, the means for exciting the material may comprise a light source arranged to emit an optical excitation signal in order to make the material emit a photoluminescent signal, or else an electrical source arranged to emit an electrical signal over a number of electrodes placed on the material in order to make the material emit an electroluminescent signal, or even a thermal source arranged to heat the material in order to make the material emit a thermoluminescent signal.

According to another aspect, provision is made for a computer program, loadable into a memory associated with a processor, and comprising code portions for implementing at least some of the steps of the proposed method on execution of said program by the processor, and a set of data representing, for example by way of compression or encoding, said computer program.

Another aspect relates to a non-transient medium for storing a program executable by computer, comprising a set of data representing one or more programs, said one or more programs comprising instructions for analysing the crystal structure of a polycrystalline semiconductor material that, on execution of said one or more programs by a computer comprising a processing unit operationally coupled to memory means and to an input/output interface module, leads the computer to perform the estimate and to generate a representation according to the proposed method.

Other particularities and advantages of the present invention will appear in the description hereinbelow of non-limiting example embodiments, with reference to the appended drawings, in which.

In the detailed description hereinbelow of embodiments of the invention, many specific details are presented to allow a fuller understanding. Nonetheless, those skilled in the art may realize that some embodiments can be put into practice without these specific details. In other cases, well-known characteristics are not described in detail to avoid pointlessly complicating the description. Moreover, certain components, devices, means and elements having one and the same function may be referenced with the same reference number in a number of figures, and the repetition of the description of these components, devices, means and elements may be in certain cases omitted or abridged.

The proposed method may advantageously be used with various types of polycrystalline semiconductor materials, such as for example polycrystalline semiconductor materials from the III-IV family (such as gallium arsenide (GaAs), indium phosphide (InP) or gallium antimonide (GaSb)), the polycrystalline semiconductor materials of the II-VI family (such as cadmium telluride (CdTe) or one of its alloys or derivatives, in which the cadmium may be partly replaced by zinc or mercury and the tellurium may be partly replaced by selenium), polycrystalline alloys with chalcopyrite structures such as CIGS, or again polycrystalline silicon. By GIGS is understood here in a general manner the $CuInSe_2$ family, or one if its derived alloys, in which copper may be replaced by silver, indium may be partly replaced by aluminium or gallium ($Cu(In, Ga)Se_2$), and the selenium may be partly replaced by sulphur or tellurium.

Furthermore, the proposed method may advantageously be used for the analysis of a sample comprising one or more polycrystalline semiconductor materials, as well as other materials. The various polycrystalline semiconductor materials contained in the sample may present distinct characteristics, particularly with regard to their crystal structure. Those skilled in the art will understand that the proposed method may be applied to only one of the materials contained in an analysed sample, or else sequentially to a number of of these materials included in the analysed sample, the various analysis parameters according to the proposed method then being fitted depending on the targeted polycrystalline semiconductor material for each crystal structure analysis, particularly by selecting the excitation wavelength of the analysed material and the detection wavelength of the luminescent signal.

Figure 1:
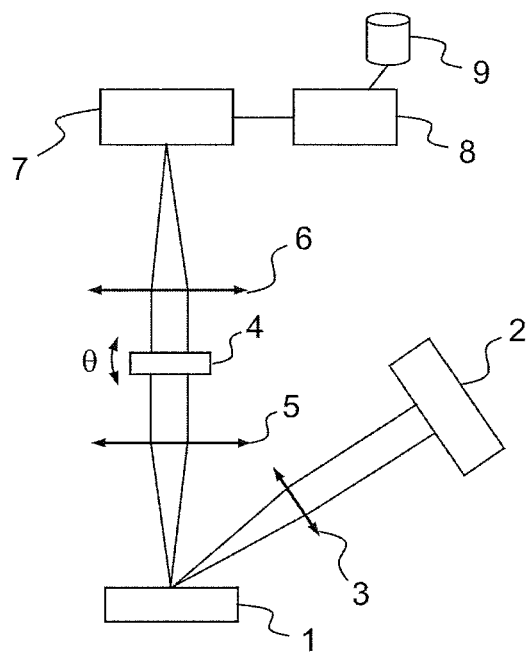
FIG. 1 is a diagram illustrating an implementation of the proposed method according to a first embodiment.

FIG. 1 illustrates an implementation of the proposed method according to a first embodiment.

FIG. 1 shows a sample (1) of polycrystalline semiconductor material to be analysed, as well as a light source (2) arranged to emit an optical excitation signal in the direction of the sample (1). This optical excitation signal is adapted in order to make the sample (1) emit a luminescent signal. The light source (2) is therefore chosen with a spectral range that corresponds to an absorption region of the analysed material. The light source (2) may for example be the laser source, or else an incoherent light source.

The excitation signal generated by the source is local, in the sense that it excites only a portion of the sample to be analysed. To obtain this local excitation it is possible to use means for focusing an excitation beam produced by the laser source, such as for example a focusing lens (3) placed between the laser source (2) and the sample (1) to be analysed. The focal length of the focusing lens is in practice chosen depending on the analysis resolution desired and on the light source used. For example, for a sample of polycrystalline CIGS material, a microscope lens of focal length 4 mm and numerical aperture 0.8 may be used in order to obtain a local excitation of a surface smaller than the size of the crystals, i.e. 1 µm. The excitation laser beam is absorbed by the sample (1), and part of the energy of the optical excitation signal is dissipated in the form of a photoluminescence signal emitted spontaneously by the excited material.

The focusing of the excitation laser beam in this embodiment enabling a spatial resolution at the centimetric to sub-micrometric scale in the local excitation of the sample (1), it is possible to define a mesh for the requirements of this data acquisition phase with a corresponding resolution. The proposed method thus makes it possible to reach high spatial resolutions (typically from 0.5 to 10 µm), for example meeting the requirements for the study of microcrystalline solar cells.

The sample (1) being composed of a semiconductor material, it has a first energy level (corresponding to an energy band called "conduction band") and a second energy level (corresponding to an energy band called "valence band"). The energy transitions of the electrons are principally made between the state of the conduction band and that of the valence band. The valence band and the conduction band are separated by an energy gap $E_{gap}$, to which is associated an energy band known as the "bandgap". This energy gap is also called bandgap energy. When the photons emitted by the light source have an energy of less than the gap $E_{gap}$, the energy transmitted to the electrons of the valence band is not enough to promote them to the conduction band, and they do not leave the valence band. The material, excited with an energy of less than the gap $E_{gap}$, is then transparent. On the other hand, when the photons emitted by the light source have an energy greater than the energy gap $E_{gap}$, they excite some of the electrons of the material with enough energy to be promoted from the valence band towards the conduction band, by creating an electron-hole pair (the "hole" being a reference to the absence in the valence band of the electron which has moved into the conduction band). The electron-hole pairs thus created recombine and emit photons according to the phenomenon of photoluminescence. The energy of the emitted photons is close to the bandgap energy.

The bandgap energy is a characteristic of the material of the sample (1) (of a value of 1.1 eV for silicon, of 1.12 eV for the material CIGS $CuInSe_2$, and of 1.65 eV for the material CIGS $CuGaSe_2$). Thus, the light source (2) is adapted to emit an energy signal greater than the energy gap $E_{gap}$ between the valence band and the conduction band which is specific to the material of the sample (1). For example, for a sample containing a polycrystalline semiconductor material of CuInGaSe2 (CIGS) type, having a gap of 1.12 eV, a single-mode laser at 2.33 ev (532 nm) is chosen as the excitation source (2).

The light signal emitted by photoluminescence is than detected and stored for various values of orientation and polarization in a data acquisition phase.

The detection of the luminescent signal is performed in a frequency band of width greater than or equal to the width of the bandgap of the analysed material. This adjustment of the detection frequency band of the luminescent signal to the characteristic bandgap width of the material targeted for analysis makes it possible to gather information on the crystalline structure of the analysed material. In this way it is possible to carry out the detection for wavelengths that are characteristic of the crystalline matrix of the analysed material.

The detection of the photoluminescent signal may for example be carried out with two detection lenses (as illustrated in FIG. 1, with the detection lenses (5) and (6)), the sample being arranged substantially in the object focal plane of the first lens. One of the advantages of this schema is the possibility of placing the polarizer (4) between the two detection lenses (5)(6). The photoluminescent signal is then detected at the output of the detection optics (5)(6) by a detector (7), which may for example be chosen from the photomultiplier type, in order to obtain the desired level of precision and sensitivity. For example, in the case of the CIGS-type sample as mentioned above, a photomultiplier of InGaAs type having an optimal spectral response in the near infrared (1000 nm>λ>1200 nm) may be chosen as detector. As a variant, a spectrometer may be used as detector (7) for implementing the proposed method, which will enable, in addition to the acquisition of data representing the intensity of the luminescent signal, the acquisition of data representing a frequency distribution (wavelength) of the intensity of the luminescent signal.

The data acquisition is thus performed by detecting, at each point of a mesh in a preset spatial region of the material, the luminescent signal for various values of orientation of polarization, thereby enabling analysis of the luminescent signal for various values of orientation of the polarization of this signal. The following paragraph describes two examples of methods of polarization analysis of the luminescent signal.

According to a first method, measurements are performed on the luminescent signal for a number of values of orientation of a linear polarizer adapted to the luminescent region of the sample, placed between the sample to be analysed and the detection optics, which are made to turn.

According to a second method, measurements are performed on the luminescent signal for a number of values of orientation of polarization by turning a wave plate (of λ/2 type) placed in front of a polarizer.

It is thus possible to proceed, at each point of the mesh, with the detection and the recording of the luminescent signal for a number of values of orientation θ of a polarizer or of a wave plate by varying the angle θ of orientation from −90° to +90°, with a step of the order of 5°. The interval of variation of the angle θ of orientation may of course be chosen differently, as can the variation step of the angle of orientation θ, depending on the characteristics of the material to be analysed and on the analytical precision required, without for all that departing from the scope of the proposed method.

A mesh of points in a spatial region of the sample to be analysed is therefore defined beforehand. Each point of the mesh is excited locally by the light source (2) in order to spontaneously emit a luminescent signal. The detection of this luminescent signal is performed on each point of the mesh for various values of orientation θ of polarization of the luminescent signal.

In order to locally excite and analyse the luminescent signal at each point of the mesh, the sample (1) is moved in the focal plane of the focusing lens (5) using a translation table. For example, in the aforementioned case of the GIGS sample, it is possible to move the sample to be analysed using a piezoelectric table referred to as an xy table.

For each point of the mesh, the detection of the luminescent signal for various values of orientation of polarization is carried out by modifying the angle θ of the polarizer, with a step chosen as a function of the desired resolution (for example of 5°). It is thus possible to detect and record an intensity value $I_{lum}(\theta)$ of the luminescent signal for a set $(\theta_i)_{i=Nmin \ldots Nmax}$ of discrete values of polarizer angle, with $\theta_{i+1}=\theta_i+\Delta\theta$, and this for each point of the mesh.

The detector (7) is equipped with a memory for recording the detected data, or as a variant with an interface towards a memory or a data processing unit (8) equipped with a memory (9) for data storage.

The phase of acquisition of the data of the luminescent signal is followed by a phase of data processing, performed for example by a data processing unit (8). The data processing comprises the measurement from data acquired by the detector (7) of one or more parameters of a sine wave model of the variations of the intensity $I_{lum}$ of the luminescent signal as a function of the angle $\theta$ of the polarizer. In a preferred embodiment of the proposed method, the sine wave model is of type $I_{lum}=A_0+\Sigma_{k=(1 \ldots K)}A_k \cdot \sin(n_k\theta+\varphi_k)$, where $I_{lum}$ denotes the intensity of the luminescent signal, $A_k$ is an amplitude parameter of the luminescent signal, $\theta$ represents the analysis angle of the polarization of the luminescent signal, $\varphi_k$ is a parameter of the phase shift of the luminescent signal with respect to a reference phase, $n_k$ is a strictly positive integer, $A_0$ (offset) is a parameter representing the minimum value of the intensity of the luminescent signal, and k is an integer summation index ranging from 1 to K. The measured value $I_{lum}$ denotes the intensity of the luminescent signal after filtering by the polarizer for the purpose of analysing the polarization at various angles. In the present embodiment, where the polarization analysis is performed for example by means of a polarizer the angle of which is made to vary, the variable $\theta$ corresponds to the angle of the polarizer. In the case where the polarization analysis is carried out for example by means of a wave plate placed in front of a polarizer and the rotation angle of which is made to vary, the variable $\theta$ corresponds to the angle of rotation of the wave plate. In both cases the variable $\theta$ corresponds to the angle of orientation of the polarization of the luminescent signal. The parameters $A_k$, $\varphi_k$, $n_k$ and/or $A_0$ (offset) are estimated by comparing the sinusoidal model to the various measured values acquired for each point of the mesh. By putting the data acquired for each point of the mesh in correspondence with the sinusoidal model, an estimation of the values of the parameters of this model is extracted which corresponds best to the acquired data. Thus, at the outcome of this data processing phase, an estimation of one or more parameters of the sinusoidal model is obtained, and this for each point of the mesh.

It is then possible, while remaining in the scope of the proposed method, to combine the obtained estimations to obtain the estimate of a combination of these parameters.

K is a natural integer greater than or equal to one, which may be chosen for example to be equal to one or two, or else greater than two depending on the modelling accuracy sought for the purposes of the analysis of the crystal structure.

It is also possible to proceed iteratively, in order to define the smallest value of K for which the model obtained allows a satisfactory fit with the experimental data. This iterative process of increment $\Delta_K$ of selection of an optimal value for K may be continued until the value $K+\Delta_K$ leads to a theoretical model less satisfactory in terms of its fit with the collected experimental data than the preceding K value.

The fitting (the term "numerical modelling" is also sometimes used) of the chosen theoretical model (in the example described, a sinusoidal model of type $I_{lum}=A_0+\Sigma_{k=(1 \ldots K)}A_k \cdot \sin(n_k\theta+\varphi_k)$) to the experimentally acquired data is performed according to correlation methods, for example the least squares method or the Mayer fitting method, in order to extract an estimate with the desired accuracy of the parameter(s) sought. The fineness of the resolution of the acquisition of data (in particular the value chosen for the increment $\Delta\theta$ of variation of the angle $\theta$ of the polarizer) at each point will allow a fitting that is more or less rapid and accurate for the estimate of the parameter(s) of the chosen model.

The fitting of the chosen theoretical model to the data acquired experimentally and the estimate of the parameter(s) of the chosen model being performed at each point of the preset mesh in the spatial region of the material (1), it is then possible to generate a representation for all of the mesh points of the values estimated for a given parameter, and therefore a mapping of the spatial variation of each of the parameters or of combinations of the latter.

In the considered example of the sinusoidal model of type $I_{lum}=A_0+\Sigma_{k=(1 \ldots K)}A_k \cdot \sin(n_k\theta+\varphi_k)$, the processing of data may enable an estimation of the value of the amplitude parameter ($A_k$), of the value of the phase shift parameter ($\varphi_k$) of the value of the frequency parameter ($n_k$), and/or of the value of the minimum value parameter $A_0$ (offset), or of a combination of a number of these parameters, and this for each point of the mesh, which makes it possible to draw up a mapping of the amplitude parameter ($A_k$), of the phase shift parameter ($\varphi_k$), of the frequency parameter ($n_k$) and/or of the minimum value parameter $A_0$ (offset), or of a combination of a number of these parameters.

More specifically, with the model proposed by way of example, $I_{lum}=A_0+\Sigma_{k=(1 \ldots K)}A_k \cdot \sin(n_k\theta+\varphi_k)$, it can be observed that for a polycrystalline CIGS material there is a correlation between the parameters $\varphi_k$ and $A_k$ and the local orientation properties of the crystal structure.

These representations of the spatial distribution of the variation in the luminescent signal as a function of the angle of the polarizer, for each of the parameters, make it possible to isolate various structural properties of the analysed material as a function of the parameter represented. For example, the amplitude $A_k$ and the phase shift $\varphi_k$ may be correlated to the orientation of the crystalline axes of the analysed material. These parameters may also be connected to the presence of crystalline defects in the material studied.

Furthermore, in order to obtain an absolute orientation of the crystalline axes of the material, a calibration of the experimental device may be made. In order to do this, it is possible to use a monocrystalline sample the crystalline orientation of which has been defined beforehand by a method of analysis such as X-ray diffraction. The analysis parameters may then be connected to said crystalline orientation of the calibration material.

In the case of the microcrystalline CIGS sample, a spatial disparity is observed in the photoluminescent intensity that has no obvious correlation with crystalline orientation. However, the representation in mapping of the $\varphi_k$ parameter reveals, for example, a mosaicity corresponding to spatial regions of a few $\mu m^2$, the size of the grains of the analysed material. Moreover, on a sample of monocrystalline CIGS, no spatial variation of the fitting parameters is observed. This makes it possible to better appreciate the fact that the methods proposed here allow among other things the polycrystalline character of the material to be revealed and the crystals to be identified.

Figure 6A:
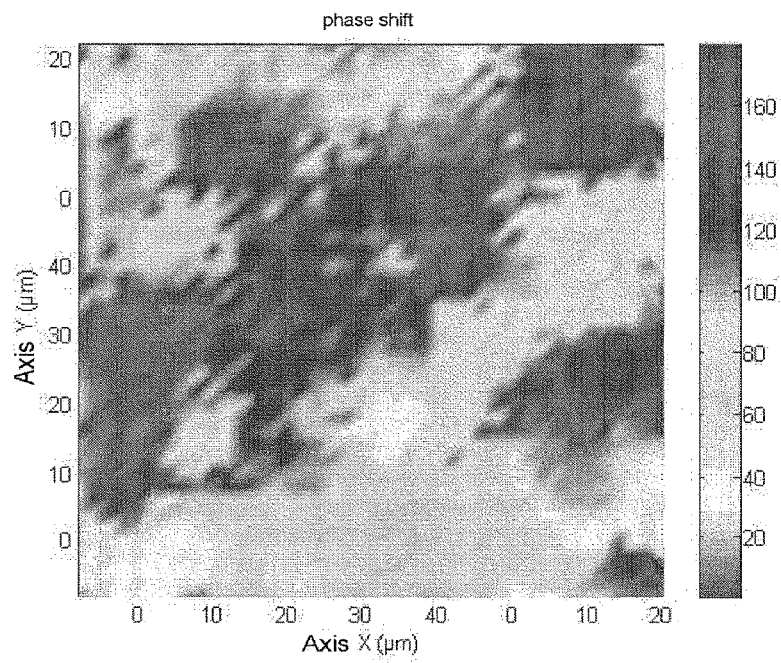
FIG. 6a shows an example of mapping of the phase shift parameter $\varphi_k$ obtained according to the proposed method for a sample based on polycrystalline CIGSe material.
Figure 6B:
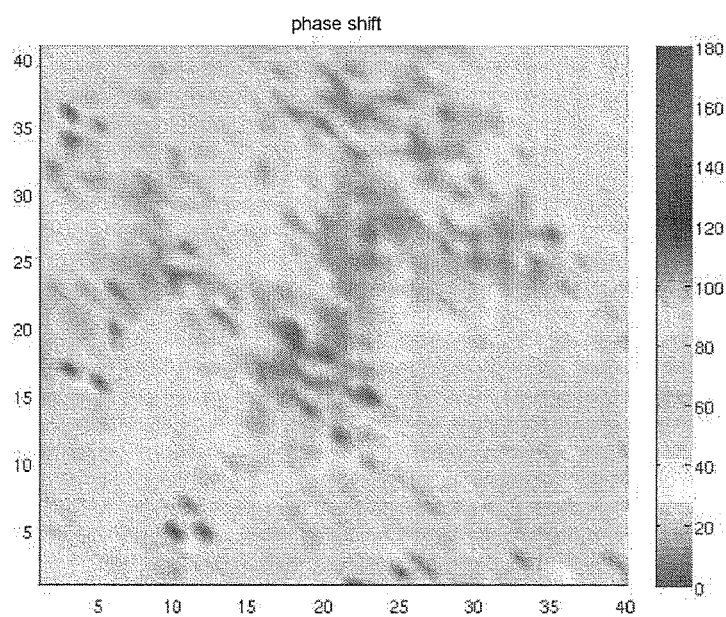
FIG. 6b shows an example of mapping of the phase shift parameter $\varphi_k$ obtained according to the proposed method for a sample based on monocrystalline CIGSe material.

FIG. 6a represents an example of mapping of the phase shift parameter $\varphi_k$ obtained according to the proposed method for a sample based on the polycrystalline material CuIn1-xGaxSe2 (CIGSe) on which spatial regions corresponding to the crystal structure of the sample may be discerned. The contrast with the mapping represented on FIG. 6b is apparent, FIG. 6b representing an example of mapping of the phase shift parameter $\varphi_k$ obtained according to the proposed method for a sample based on monocrystalline CIGSe material. The monocrystal structure of the analysed sample in FIG. 6b is revealed by the uniformity of the mapping of the phase shift parameter, a uniformity that is not observed in the mapping of FIG. 6a.

This method of analysis by photoluminescence with local excitation makes it possible to achieve very fine spatial resolutions, typically less than 1 µm, without forbidding work with larger resolutions, millimetric for example, or else, typically, corresponding to an analysis surface on the material of the order of 100 µm². The dimension of a grain in a polycrystalline CIGS being for example typically of the order of the µm, the accessible resolution opens up new possibilities for the analysis of microcrystalline materials such as GIGS, a thin film photovoltaic market in the middle of a boom. It is furthermore suitable for analysis (whether it be for purposes of material characterization or of detection of defects for the application envisaged) of thin films of materials, of a thickness typically less than 3 µm, and used in photovoltaic products, which can exhibit at their surface a crystal structure with micrometric dimensions (without this necessarily always being the case). It is thus possible to characterize with great accuracy the thin films of photovoltaic cells during the film growth process, in order to ensure, for example, that the growth of the film has been achieved with the desired properties of orientation of the crystal structure.

The data processing unit (8) may be a computer, a network of computers, or another apparatus containing a processor, a memory, a data storage unit (9), and other associated hardware units such as a network interface and a medium reader for reading and writing to a removable storage medium (not shown in the figure). The removable storage medium may, for example, be a compact disc (CD), a digital video/multipurpose disc (DVD), a flash drive, etc. The removable storage medium contains instructions which, when they are executed by the data processing unit (8), cause the data processing unit (8) to perform the data acquisition and/or processing phases of the examples of implementation of the proposed method described in these pages. The removable storage medium may comprise instructions for implementing and for executing an analysis engine (or analyser) configured to perform the data processing phase. Certain parts of the analysis engine may be stored as instructions on a given instance of the removable storage medium, a removable device or a local data storage (9), in order to be loaded into the memory for execution by the processor. Specifically, software instructions or a program code readable by computer for performing embodiments may be stored, temporarily or permanently, in totality or in part, on a non-transitory computer-readable medium such as a compact disc (CD), a local or remote storage device, a local or remote memory, a floppy disk, or any other computer-readable storage device.

Although the analysis engine is described in the form of a program residing in the memory, the analysis engine may be implemented in hardware form, as an application specific integrated circuit (ASIC) or in the form of a combination of hardware and software elements.

Figure 2:
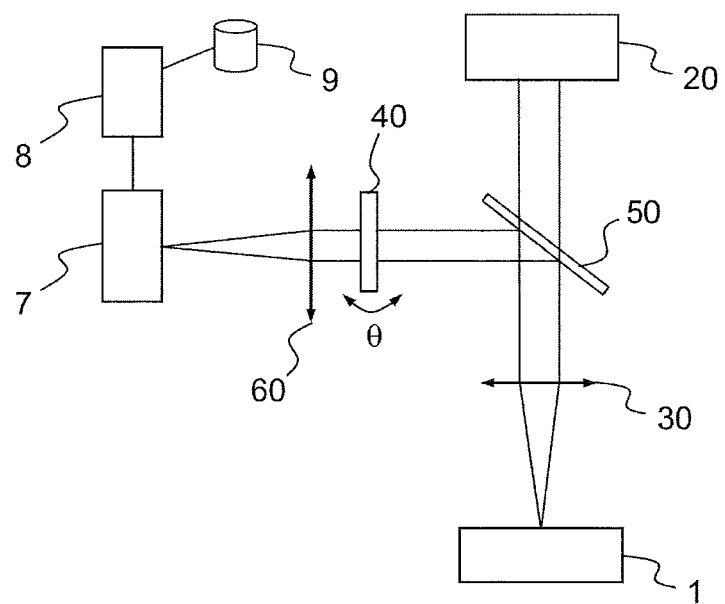
FIG. 2 is a diagram illustrating another implementation of the proposed method according to the first embodiment.

FIG. 2 shows a variant implementation of the proposed method according to the first embodiment, in which a dichroic mirror is used.

The sample (1) of the polycrystalline semiconductor material to be analysed is excited by an excitation signal emitted by a light source (20) (for example a transverse monomode laser) and focused on the point of analysis by a focusing lens (30). This optical excitation signal is adapted in order to make the sample (1) emit a luminescent signal. It is furthermore adapted to traverse a dichroic mirror (50) placed between the luminescent signal and the focusing lens (30). The light source (20) may for example be a laser source, or else an incoherent light source.

The photoluminescent signal is directed towards the detector (7) by means for detecting optics (30), (50) and (60). In particular, the dichroic mirror (50) is adapted and positioned in order to separate the photoluminescent signal from the excitation signal. A polarizer (40) is placed between the mirror (50) and the second detection lens (60), in order to be able to analyse the photoluminescent signal for various values of orientation θ of the polarizer.

This variant embodiment of the proposed method using a dichroic mirror furthermore makes it possible to use a method of local excitation and of analysis of the luminescent signal at each point of the mesh other than that described above. Specifically, it is possible as an alternative to the use of a translation table, to move the laser excitation beam using orientable mirrors (for example of piezoelectric type) placed between the detection/excitation optics and the focusing lens (30).

Figure 3:
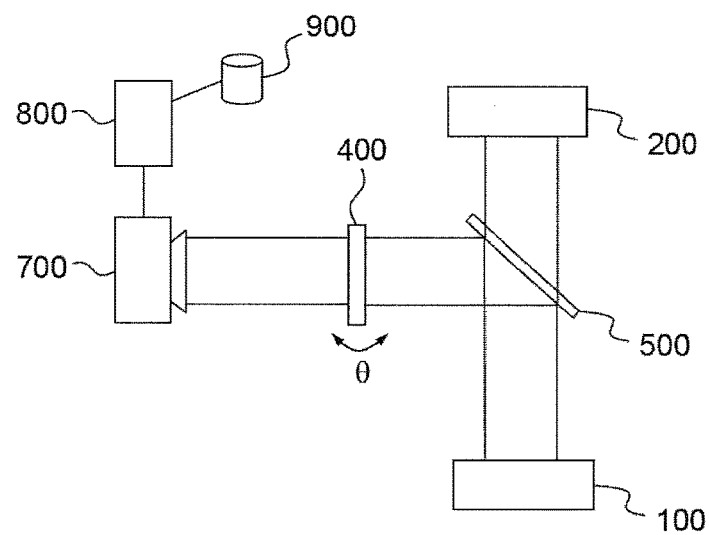
FIG. 3 is a diagram illustrating an implementation of the proposed method according to a second embodiment.

FIG. 3 illustrates an implementation of the proposed method according to a second embodiment.

FIG. 3 shows a sample (100) of polycrystalline semiconductor material to be analysed, and a light source (200) arranged to emit an optical excitation signal in the direction of the sample (100). This optical excitation signal is adapted in order to make the sample (100) emit a luminescent signal. The light source (200) is thus chosen with a spectral range that corresponds to an absorption region of the material analysed. The light source (200) may for example be a laser source, or else an incoherent light source.

The excitation signal generated by the source is global in the sense that it excites almost all of the surface of the region to be analysed. There is therefore no use in this embodiment of the proposed method of any means of focusing the excitation signal in order to locally excite only a given region of the surface of the material to be analysed. As in the embodiment explained above, the light source (200) is adapted to emit a signal of energy greater than the energy gap $E_{gap}$ between the valence band and the conduction band, which is specific to the sample material (100).

Thus, in this embodiment, the sample is excited in a global manner and the image of the luminescence is recorded by way of a camera (700), preferably a digital camera.

The detection of the photoluminescent signal may for example be performed as illustrated in FIG. 3 by placing a dichroic mirror (500), adapted and positioned in order to reflect the photoluminescent signal. A polarizer (400), of which the orientation is varied, is placed in front of the camera (700) in such a way that the latter detects the photoluminescent signal filtered by the polarizer (400), and this for different orientations of the polarizer (400). The photoluminescent signal is then detected by the camera (700), which may for example by chosen to be of the CCD type. Other types of cameras, such as for example infrared (IR) detection cameras, using InGaAs technology, or else CMOS detector cameras, may also be used for implementing this embodiment of the proposed method.

The camera (700) is chosen so that it is capable of, and is configured to perform, the detection of the luminescent signal in a frequency band of width greater than or equal to the width of the bandgap of the analysed material. In this embodiment, the wavelengths that are characteristic of the crystalline matrix of the analysed material are detected by means of a camera.

In the same way as the embodiments previously described, the acquisition of data is performed by detecting, at each point of a mesh in a preset spatial region of the material, the luminescent signal for various values of orientation of polarization, with the sole difference that the mesh may advantageously be chosen, in this example embodiment, to correspond to the points on the sensor of the camera (700).

In this way, the image sensed by the camera (700) is detected and recorded (at each point of the mesh), the image being generated by detecting the luminescent signal, for a number of values of orientation θ of the polarizer (400) by varying the angle of orientation θ from −90° to +90°, with an increment of the order of 5°. The interval of variation of the angle of orientation θ of the polarizer may of course be chosen differently, likewise the increment of variation of the angle of orientation θ, depending on the characteristics of the analysed material and on the desired accuracy of analysis, without departing from the scope of the proposed method.

It will be noted that the examples of methods of analysis of polarization of the luminescent signal described above (variation of the orientation of a linear polarizer or variation of the orientation of a wave plate placed in front of a polarizer) are applicable to the present embodiment of the proposed method.

For each point of the mesh, detection of the luminescent signal for various values of orientation of polarization is therefore performed, for example, by modifying the angle θ of the polarizer, with an increment chosen depending on the desired resolution (for example of 5°). It is thus possible to detect and record a set of images corresponding to the luminescent signal for a set $(\theta_i)_{i=Nmin\_Nmax}$ of N discrete values of polarizer angle, with $\theta_{i+1} = \theta_i + \Delta\theta$.

In one example of implementation of the proposed method according to this second embodiment, a hyperspectral imager is placed in front of the camera (700) in order to acquire, in addition to the data representing the intensity of the luminescent signal, data representing a frequency distribution of the intensity of the luminescent signal.

The acquired data take the form of a set of N images $(Im_i)_{i=1\_N}$, each corresponding to the photoluminescent signal emitted by the analysed material over a preset region of analysis of the material, for a value $\theta_i$ of orientation of polarization.

The camera (700) is equipped with a memory for recording the detected images, and is connected by means of a data exchange interface to a data processing unit (800) which is also equipped with a memory (900) for data storage.

The phase of acquisition of luminescent signal data is followed by a data processing phase, performed for example by a data processing unit (800), which comprises the measurement on the acquired data of one or more parameters of a sinusoidal model of the variations in intensity $I_{lum}$ of the luminescent signal as a function of the orientation θ of polarization. The processing of data performed by the data processing unit (800) corresponds to that described above in the context of implementing the proposed method according to the first embodiment.

This method of analysis by photoluminescence with global excitation constitutes an advantageous compromise between speed of execution, simplicity of implementation and fineness of analysis. Although global excitation does not make it possible to reach resolutions as fine as those achieved with local excitation, it offers a speed and simplicity of implementation that renders it particularly well-suited to its implementation within a mass production process. Furthermore, like the method explained previously, this method of analysis by photoluminescence with global excitation may be implemented during manufacture, for example in the film growth phase for a photovoltaic product, thereby allowing, at an advanced stage of the manufacture, certain defects, correctable or otherwise, to be detected and thus substantial manufacturing costs to be avoided.

Figure 4:
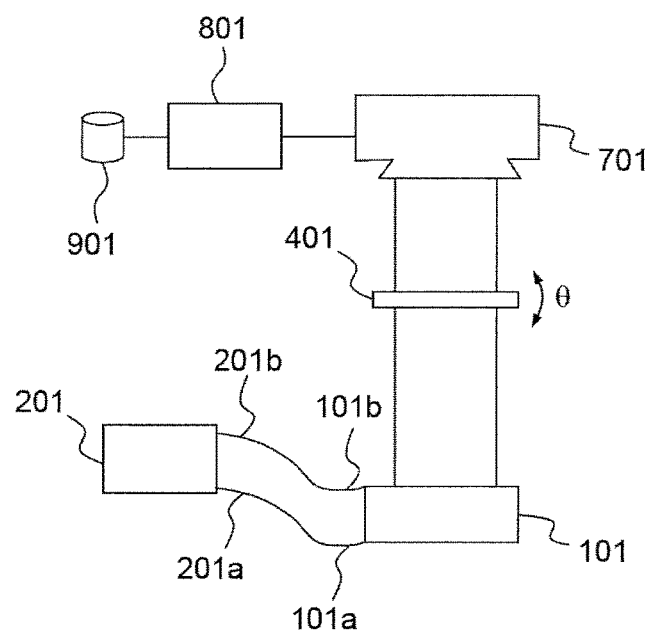
FIG. 4 is a diagram illustrating an implementation of the proposed method according to a third embodiment.

FIG. 4 illustrates an implementation of the proposed method according to a third embodiment.

FIG. 4 shows a sample of photovoltaic cell (101) comprising a polycrystalline semiconductor material to be analysed, as well as an electrical current generator (201) the outputs (201a; 201b) of which are electrically connected to the electrodes (101a; 101b) of the cell (101). The electrical signal delivered by the generator (201) is adapted in order to make the photovoltaic cell (101) emit an electroluminescent signal.

The electrical excitation signal is adapted so that the polycrystalline semiconductor material of the cell (101) is excited and spontaneously emits an electroluminescent signal over all of the surface of the excited material. In particular, the electrical source (201) is adapted to generate an electrical excitation signal of energy greater than the energy gap $E_{gap}$ between the valence band and the conduction band, which is specific to the polycrystalline semiconductor material of the cell (101) to be analysed.

The following steps of the proposed method described above (as well as their variants) in the context of an excitation by an optical signal are applicable to the present embodiment, which provides for generating an electroluminescent signal.

For example, and as illustrated in FIG. 4, it is possible to record the electroluminescent signal emitted by the material by way of a camera (701), preferably a digital camera. It is furthermore possible to place in front of the camera (701) a polarizer (401), the orientation of which is varied so that the camera (701) detects the electroluminescent signal for various orientations of polarization, as described above. The electroluminescent signal is then detected by the camera (701), which may for example be chosen to be of the CCD type. Other types of camera, such as for example infrared detection cameras (IR), using InGaAs technology, or else CMOS detector cameras, may also be used to implement this embodiment of the proposed method.

Here again, the camera (701) is chosen so that it is capable of, and is configured to perform, the detection of the luminescent signal in a frequency band of width greater than or equal to the width of the bandgap of the analysed material. In this embodiment the wavelengths that are characteristic of the crystalline matrix of the analysed material are detected by means of a camera.

The detection of the electroluminescent signal, the acquisition of the electroluminescent signal data and the processing of the acquired data may be performed according to the corresponding steps of one of the embodiments described previously for a photoluminescent signal. This method of analysis by electroluminescence is particularly well-suited to the analysis of photovoltaic cells once manufactured, particularly in the context of tests for measuring manufacturing quality and conformity with expected performance.

Figure 5:
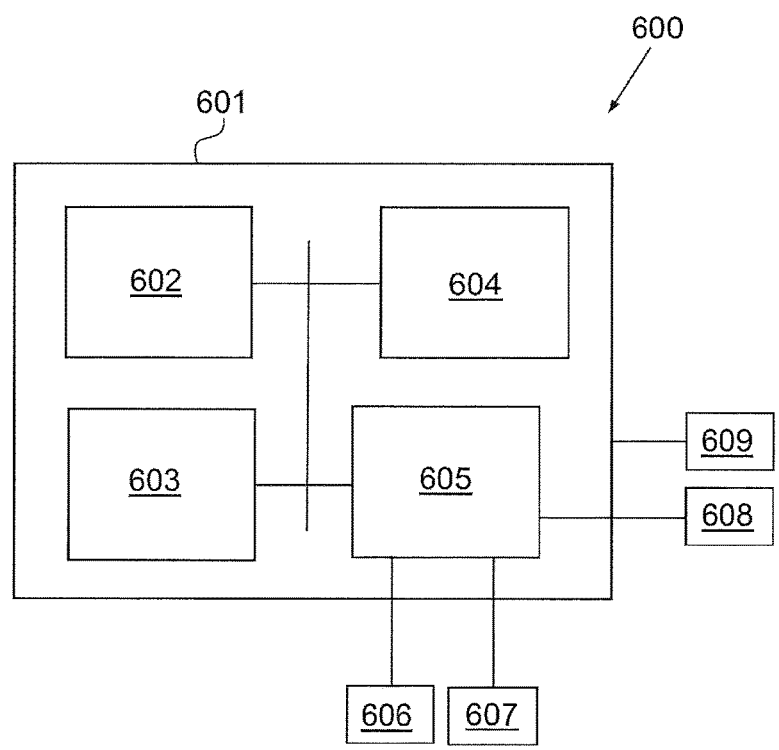
FIG. 5 shows a computer system for implementing the proposed method.

Modes of carrying out analysis of the crystal structure of a polycrystalline semiconductor material may be, at least partly, implemented on practically any type of computer, independently of the platform used. For example, as shown in FIG. 5, a computer system (600), which may correspond to the data processing units (8)(800) and memories (9)(900) shown in FIGS. 1 to 4 or be coupled operationally to these elements, comprises a data processing unit (601) which comprises one or more processors (602), such as a central unit (CPU) or another hardware processor, an associated memory (603) (for example, a live memory (RAM), a cache memory, a flash memory, etc.), a storage device (604) (for example, a hard disk, an optical disk such as a CD or a DVD, a flash memory key, etc.), and many other typical elements and functionalities of current computers (not shown).

The data processing unit (601) also comprises an input/output interface module (605) which controls the different interfaces between the unit (601) and the input/output means of the system (600). The system (600) may indeed also comprise input means, such as a keyboard (606), a mouse (607) or a microphone (not shown). Furthermore, the computer (600) may comprise output means, such as a monitor (608) (for example, a liquid crystal display (LCD) monitor, a plasma display monitor or a cathode ray tube (CRT) monitor). The computer system (600) may be connected to a network (609) (for example, a local network (LAN), a wide area network (WAN) such as the Internet, or any other similar type of network) by way of a network connection interface (not shown). Those skilled in the art may realize that there are many different kinds of computer systems (for example, a desktop computer, a laptop computer, or any other computer system capable of executing instructions readable by computer), and the input and output means mentioned above may take other forms, currently known or developed subsequently.

In general, the computer system (600) comprises at least the minimal means for processing, for input and/or output necessary to put into practice one or more embodiments of the analysis method proposed. For example, the processor (602) may be configured to execute a computer program comprising portions of code for implementing an analyser, configured to estimate one or more characteristic data of the modulation of the luminescent signal and to generate a representation of the characteristic data according to the various embodiments of the proposed analysis method. The storage device (604) chosen will preferably be capable of storing the data corresponding to the signal detected for each point of the mesh.

Although the analyser configured to estimate and generate the representation is described in the form of a software package, it may be implemented in hardware form or in the form of a combination of hardware and software instructions.

The computer system (600) is furthermore advantageously operationally coupled to the luminescent signal detector in order to store in memory the acquired data with a view to processing them according to the analysis method provided by the computer system (600). As a variant, provision may also be made to store, in memory (604), data to be processed by any known means, not necessarily implying a direct connection between the detector used for the detection of the luminescent signal and the computer system (600).

Furthermore, those skilled in the art may realize that one or more elements of the aforementioned computer system (600) may be found at a remote location and be connected to other elements on a network. Moreover, one or more embodiments may be implemented on a distributed system containing a number of nodes, where each portion of the implementation (for example, various components of the two-domain analysis tool) may be situated on a different node inside the distributed system. In one or more embodiments, the node corresponds to a computer system. As a variant, the node may correspond to a processor with an associated physical memory. The node may also correspond to a processor with a partitioned memory and/or partitioned resources. Furthermore, software instructions for performing one or more embodiments may be stored on a computer-readable medium such as a compact disc (CD), a floppy disk, a tape, or any other computer-readable storage device.

Depending on the embodiment chosen, certain operations, actions, events or functions of each of the methods described in the present document may be performed or occur in a different order to that in which they have been described, or may be added or combined or they may even not be performed or may not occur, depending on the circumstances. Furthermore, in certain embodiments, certain operations, actions or events are performed or occur concurrently and not sequentially.

Although the analysis of the crystal structure of a polycrystalline semiconductor material has been described with respect to a limited number of embodiments, those skilled in the art having become familiar with the present record may realize that other embodiments may be considered without departing from the definition of the analysis of crystal structure of a polycrystalline semiconductor material such as described in the present pages. The definition of the analysis of crystal structure of a polycrystalline semiconductor material is limited only by the appended claims.

The invention claimed is:

1. A method for analyzing the crystal structure of a polycrystalline semiconductor material comprising:
   exciting the material in order to make the material emit a luminescent signal;
   detecting, at each point of a mesh in a preset spatial region of the material, the luminescent signal at a variable polarization angle, in a frequency band of width greater than or equal to the width of the bandgap of the material;
   estimating, at each point of the mesh in the preset spatial region of the material, from the signal detected for said point of the mesh, a data characteristic of the modulation of the luminescent signal, modelled by a sum of sine waves, as a function of the polarization angle;
   generating a representation of the characteristic data over all of the points of the mesh in the preset spatial region; and
   determining from the representation at least one characteristic of the polycrystalline semiconductor material selected from the group consisting of defect presence, crystalline orientation, and size of crystalline grains.

2. The method according to claim 1, in which the model of the modulated luminescent signal is of the form:

$$I_{lum} = A_0 + \sum_{k=\{1\ ...\ K\}} A_k \cdot \sin(n_k \theta + \varphi_k),$$

where $I_{lum}$ represents the intensity of the luminescent signal, $A_k$ is an amplitude parameter of the luminescent signal, $\theta$ represents the analysis angle of the polarization of the luminescent signal, $\varphi_k$ is a parameter of the phase shift of the luminescent signal with respect to a phase reference, $A_0$ a parameter representing the minimum value of the intensity of the luminescent signal, $n_k$ being a strictly positive integer, and k is a natural integer summation index ranging from 1 to K, and in which the estimated characteristic data corresponds to the amplitude, phase shift, frequency and/or minimum value parameter, or to a combination thereof.

3. The method according to claim 1, wherein the luminescent signal is detected by a camera, the preset spatial region mesh on the material corresponding by choice with points on the sensor of the camera.

4. The method according to claim 1, wherein exciting the material comprises the optical excitation of the material with a light source to make the material emit a photoluminescent signal.

5. The method according to claim 1, wherein exciting the material comprises the electrical excitation of the material with an electrical source over a number of electrodes placed on the material in order to make the material emit an electroluminescent signal.

6. The method according to claim 1, wherein exciting the material comprises heating the material with a thermal source to make the material emit a thermoluminescent signal.

7. A system for analyzing the crystal structure of a polycrystalline semiconductor material, comprising:
 a means for exciting the material, arranged to excite the material in order to make the material emit a luminescent signal;
 a means for detecting, at each point of a mesh in a preset spatial region of the material, the luminescent signal at a variable polarization angle, in a frequency band of width greater than or equal to the width of the bandgap of the material;
 a data processing unit, comprising:
 a computer processor operationally coupled to memory means and to an input/output interface module, the memory means being configured to store data corresponding to the signal detected for each point of the mesh;
 an analyser configured to:
 estimate, at each point of the mesh in the preset spatial region of the material, from the signal detected for said point of the mesh, a data characteristic of the modulation of the luminescent signal, modelled by a sum of sine waves, as a function of the polarization angle;
 generate a representation of the characteristic data over all of the points of the mesh in the preset spatial region; and
 determine from the representation at least one characteristic of the polycrystalline semiconductor material selected from the group consisting of defect presence, crystalline orientation, and size of crystalline grains.

8. The analyzing system according to claim 7, in which the analyser is furthermore configured to estimate a characteristic data as a function of a model of the modulated luminescent signal of the form:

$$I_{lum} = A_0 + \sum_{k=\{1 \ldots K\}} A_k \cdot \sin(n_k \theta + \varphi_k),$$

where $I_{lum}$ represents the intensity of the luminescent signal, $A_k$ is an amplitude parameter of the luminescent signal, $\theta$ represents the analysis angle of the polarization of the luminescent signal, $\varphi_k$ is a parameter of the phase shift of the luminescent signal with respect to a phase reference, $A_0$ a parameter representing the minimum value of the intensity of the luminescent signal, $n_k$ being a strictly positive integer, and k is an integer summation index ranging from 1 to K, and in which the estimated characteristic data corresponds to the amplitude, phase shift, frequency and/or minimum value parameter, or to one of their combinations.

9. The analyzing system according to claim 7, wherein the detecting means comprises a camera, the preset spatial region mesh on the material corresponding by choice with points on the sensor of the camera.

10. The analyzing system according to claim 7, wherein the means for exciting the material comprises a light source arranged to emit an optical excitation signal in order to make the material emit a photoluminescent signal.

11. The analyzing system according to claim 7, wherein the means for exciting the material comprises an electrical source arranged to emit an electrical signal over a number of electrodes placed on the material in order to make the material emit an electroluminescent signal.

12. The analyzing system according to claim 7, wherein the means for exciting the material comprises a thermal source arranged to heat the material to make the material emit a thermoluminescent signal.

13. A non-transitory computer readable storage medium for storing a program executable by computer, comprising:
 a set of data representing one or more programs, said one or more programs comprising instructions for analysing the crystal structure of a polycrystalline semiconductor material that, on execution of said one or more programs by a computer comprising a processing unit operationally coupled to memory and to an input/output interface module, causes the computer to perform the estimate and to generate a representation according to the method of claim 1.

* * * * *